United States Patent [19]

Oda et al.

[11] 3,998,877
[45] Dec. 21, 1976

[54] PROCESS FOR PREPARING METHACRYLIC ACID

[75] Inventors: Yoshio Oda; Keiichi Uchida; Takeshi Morimoto; Seisaku Kumai, all of Yokohama, Japan

[73] Assignee: Asahi Glass Company, Ltd., Tokyo, Japan

[22] Filed: Mar. 31, 1975

[21] Appl. No.: 563,472

[30] Foreign Application Priority Data

| | | |
|---|---|---|
| Apr. 2, 1974 | Japan | 49-36597 |
| Apr. 2, 1974 | Japan | 49-36598 |
| July 2, 1974 | Japan | 49-74971 |

[52] U.S. Cl. .......................... 260/530 N; 252/435; 252/437
[51] Int. Cl.$^2$ ........................................ C07C 51/32
[58] Field of Search ............... 260/530 N; 252/435, 252/437

[56] References Cited

UNITED STATES PATENTS

| | | | |
|---|---|---|---|
| 3,795,703 | 3/1974 | Nuna et al. | 260/530 N |
| 3,865,873 | 2/1975 | Ada et al. | 260/530 N |
| 3,875,220 | 4/1975 | White et al. | 260/530 N |

*Primary Examiner*—Vivian Garner
*Attorney, Agent, or Firm*—Oblon, Fisher, Spivak, McClelland & Maier

[57] ABSTRACT

Methacrylic acid is prepared by reacting methacrolein with molecular oxygen in the presence of a catalyst comprising (a) molybdenum, (b) phosphorus, (c) at least one element selected from the group consisting of thallium and cesium, (d) at least one element selected from the group consisting of vanadium, zirconium, tin, niobium, nickel, tantalum and iron, and (e) oxygen.

7 Claims, No Drawings

PROCESS FOR PREPARING METHACRYLIC ACID

BACKGROUND OF THE INVENTION

1. Field of the Invention

This invention relates to a process for preparing methacrylic acid by the catalytic vapor phase oxidation of methacrolein characterized mainly by the use of novel catalysts.

2. Description of the Prior Art

Many catalysts have already been proposed which are useful for the preparation of unsaturated carboxylic acids having from three to four carbon atoms by the catalytic vapor phase oxidation of the corresponding unsaturated aldehydes with molecular oxygen. Some of these are excellent for preparing acrylic acid from acrolein and have been used for the production of acrylic acid on a large scale. Various catalysts for preparing methacrylic acid from methacrolein have also been proposed. However, methacrylic acid has not been produced commercially from methacrolein by use of these catalysts because of the low yield and/or the relatively short lifetime of the catalysts. The former defect occurs because methacrolein has relatively high activity compared to acrolein. Consequently, in the oxidation condition, it is more readily subject to complete oxidation to carbon monoxide and carbon dioxide rather than to partial oxidation to the desired product, whereby the yield of the product is low and the development of an appropriate catalyst is difficult. As a result it would be highly desirable to produce a catalyst mixture for commercially preparing methacrylic acid.

SUMMARY OF THE INVENTION

Accordingly, it is one object of this invention to provide a process for preparing methacrylic acid from methacrolein in high yields so as to enable commercial production thereof.

Briefly, this and other objects of the present invention as hereinafter will become apparent from the discussion below have been attained by a process for preparing methacrylic acid by the oxidation of methacrolein with molecular oxygen in the vapor phase in the presence of a catalyst consisting essentially of (a) molybdenum, (b) phosphorus, (c) at least one element selected from the group consisting of thallium and cesium, (d) at least one element selected from the group consisting of vanadium, zirconium, tin, niobium, nickel, tantalum and iron, and (e) oxygen.

DETAILED DESCRIPTION OF THE PREFERRED EMBODIMENTS

The catalysts of the present invention possess the desired catalytic activity and long life only when they contain all of the essential components. If the catalysts lack one or more of the essential components, the catalyst activity is very low. This results in small amounts of product methacrylic acid and short lifetime for the catalysts. Thus, catalysts other than those of the above mentioned combination are unsatisfactory for commercial applications. When the catalysts of this invention contain all of the essential components, they have very good catalytic activity and long lives.

The preferred catalysts of the invention are characterized by an empirical formula which in part contains 12 molybdenum atoms as follows:

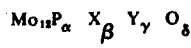   (1)

wherein X is thallium and/or cesium; Y is vanadium, zirconium, tin, niobium, nickel, tantalum and/or iron; $\alpha$ is a number from 0.1 to 3; $\beta$ is a number from 0.1 to 7; $\gamma$ is a number from 0.1 to 7; and $\delta$ is determined by the oxidation states of the other elements. In addition to the essential components described above, the catalysts of the invention may contain at least one element selected from the group consisting of tungsten, cobalt, indium, manganese, cadmium, barium and selenium. Thus, the activity of the catalyst is further improved. When the catalyst of the invention contains the optional components above, the preferred empirical formula may be expressed as follows:

   (2)

wherein X is at least one element selected from Tl and Cs; Y is at least one element selected from V, Zr, Sn, Nb, Ni, Ta and Fe; Z is at least one selected from W, Co, In, Mn, Cd, Ba and Se; $\alpha$ is a number from 0.1 to 3; $\beta$ is a number from 0.1 to 9; $\gamma$ is a number from 0.1 to 7; $\epsilon$ is a number from 0.1 to 7; $\delta$ is determined by the oxidation state of the other elements. Preferred embodiments of the catalyst may be expressed by the following formulas:

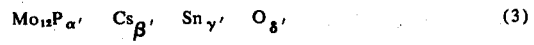   (3)

wherein $\alpha' = 0.1 - 3$; $\beta' = 0.2 - 9$; $\gamma' = 0.1 - 7$; $\delta' =$ about 36 - 100; in the highest oxidation states of elements, preferably, $\alpha' = 0.5 - 5$; $\beta' = 0.5 - 5$; $\gamma' = 0.3 - 5$.

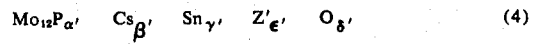   (4)

wherein $\alpha'$, $\beta'$ and $\gamma'$ are defined above, and Z' is selected from Ni, Co, Fe, V, Nb, Se, W and In; $\epsilon' = 0.1 - 7$ preferably $0.3 - 5$; $\delta'$ is determined by the oxidation state of the other elements and is about 36 - 130 when the elements are in their highest oxidation states.

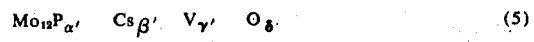   (5)

wherein $\alpha'$, $\beta'$, $\gamma'$ and $\delta$ are defined above.

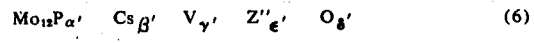   (6)

wherein Z'' is selected from W, Zr, Co, Ni, Se, Fe, Ba, In, Nb and Ta; and $\alpha'$, $\beta'$, $\gamma'$ and $\delta'$ are defined above.

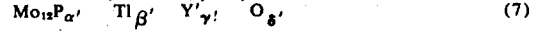   (7)

wherein Y' is at least one element selected from the group consisting of Zr, Ni, Nb, Ta, Ba and In; and $\alpha'$, $\beta'$, $\gamma'$ and $\delta'$ are defined above.

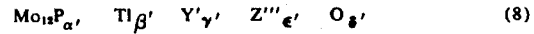   (8)

wherein Z''' is at least one element selected from the group consisting of Fe, V, Se and Sn; and $\alpha'$, $\beta'$, $\gamma'$, $\epsilon'$ and $\delta'$ are defined above. Suitable sources of starting materials of each component for use in the preparation of the catalysts include: For molybdenum-ortho, meta, or paramolybdic acid, ortho, meta or paramolybdates, heteropolymolybdic acid, heteropolymolybdates, molybdenum oxide and the like; For phosphorus-phorphoric acid, phosphates, polyphosphoric acid, polyphosphates and the like. Phosphomolybdic acid or phosphomolybdates may effectively be used as a common starting material for both the molybdenum and the phosphorus compounds. For cesium — cesium nitrate, cesium carbonate, cesium chloride and the like; For thallium — thallium nitrate, thallium carbonate and the like; For tin — stannous chloride, stannic chloride, stannic oxide and the like; For vanadium — vanadium pentaoxide, ammonium methavanadate and the like; For tungsten — tungsten trioxide, tungstic acid, salts of tungstic acids and the like; For indium — indium oxide, indium nitrate and the like; For niobium — niobium oxide, niobium hydroxide, niobium oxalate and the like; For tantalum — tantalum pentaoxide and the like; For selenium — selenic acid, selenious acid, selenium oxide and the like; For iron — ferric nitrate, ferric oxide, ferric chloride and the like; For cobalt — cobalt nitrate, cobaltic oxide and the like; For nickel —nickel nitrate, nickel chloride, nickel oxide and the like; For zirconium — zirconium oxide, zirconil nitrate and the like; and for barium — barium oxide, barium nitrate and the like.

The catalysts of the invention may be prepared from the sources of the above-mentioned elements by various methods, such as the concentrating-drying method or the coprecipitation method. Preferably, the catalyst is prepared by the following method. The sources of the elements molybdenum, phosphorus, cesium and/or thallium are uniformly mixed in slurry form with a medium such as water. The slurry is preferably kept at a pH of lower than 10.0, preferably lower than 6.0. at 60°– 110° C for 3–6 hours for aging. In the slurry, the sources of any other desirable elements are also mixed. The latter sources can be added to the surry before the aging step if desired, e.g., when the source is insoluble in water such as for an oxide of an element. The resulting slurry is concentrated and dried. The dried product is preferably calcined in air at a temperature of from 150° to 500° C, preferably 200° to 420° C for about 1 to about 48 hours. The calcined product is then ground to 35 to 100 mesh and is suitable for use. The prepared catalyst preferably has a specific surface area of 0.1 to 50 m²/g.

The structure of the catalyst may be a homogeneous mixture of the oxides of all the components, or a compound or complex formed by means of the mutual reaction of the salts of molybdenum and phosphorus with the oxides of the other components. In particular, it is found that when the catalyst has a structure composed of cesium or thallium phosphomolybdate, it has superior catalytic activity and a longer life than conventional catalysts.

In order to reduce cost and to improve the physical properties of the catalysts, they are preferably supported on a carrier. Suitable substrates include silica, silica containing materials, titania, alumina, silicon carbide and the like. It is preferred to use a carrier having a relatively large pore radius. The amount of the carrier used is preferably in the range of 30 – 97% by weight based on the supported catalyst. The catalyst can be supported on the carrier by the conventional dipping or blending methods.

In the preparation of methacrylic acid from methacrolein, the reaction temperature may vary from 230° to 450° C, preferably 250° to 380° C. The reaction pressure may vary from 0.5 to 40 atmospheres absolute, preferably from about 1 to 10 atmospheres absolute. When the reaction pressure is at the high end of the indicated range, the reaction temperature may be somewhat lower within the indicated range. Contact time for the reactants and the catalysts usually varies from 0.2 to 30 seconds preferably 1 to 20 seconds. The molecular ratio of oxygen to methacrolein in the feed gas usually varies from 1 : 10 to 10 : 1, preferably from 1 : 3 to 3 : 1. Suitable sources of oxygen include those which introduce molecular oxygen into the reaction. Air is preferred because of its economy. Steam may be added to the gaseous reaction mixture thereby improving the yield of methacrylic acid. The concentration of the steam may vary from 2 to 80% preferably from 10 to 50% of the volume of the feed. In addition, nitrogen, saturated hydrocarbons such as methane, ethane, propane, butane and the like or other inert gases may also be added to the gaseous mixture. Suitable reactors for the vapor phase oxidation reaction include a fixed-bed type reactor and a fluidized-bed type reactor and the like. The operation can be continuous or batch. The methacrylic acid may be recovered from the reaction products by any conventional method. Suitable separate techniques include condensation and/or extraction followed by distillation.

In accordance with the process of the invention, the industrial production of methacrylic acid from methacrolein is advantageously attained. Thus in turn enables industrial production of methacrylate (MMA) which is produced from methacrylic acid, without the need for employment of conventional processes such as the cyanohydrin method which possess several drawbacks, e.g., pollution effects.

Having generally described the invention, a more complete understanding can be obtained by reference to certain specific examples, which are intended for purposes of illustration only and are not intended to be limiting unless otherwise specified.

The following definitions are used in the Examples for the conversion percentage of acetic acid;

$$\text{Conversion \%} = \frac{\text{total reacted methacrolein (moles)}}{\text{methacrolein in the feed (moles)}} \times 100$$

$$\text{Selectivity of methacrylic acid (\%)} = \frac{\text{methacrylic acid in the effluent (moles)}}{\text{total reacted methacrolein (moles)}} \times 100$$

$$\text{Selectivity of acetic acid (\%)} = \frac{\text{acetic acid in the effluent (moles)}}{\text{total reacted methacrolein (moles)}} \times 100 \times \tfrac{1}{2}$$

EXAMPLE 1

A solution of 9.8 g of cesium nitrate, 2.0 g of ammonium nitrate in 50 cc of water was added with stirring to a solution of 58 g of phosphomolybdic acid ($P_2O_5 \cdot 24 MoO_3 \cdot 48 H_2O$) dissolved in 50 cc of water. A solution of 5.6 g of stannous chloride dissolved in 20 cc of conc. HCl and 40 cc of water was added to the resulting solution. The mixture was heated with stirring to form a slurry. The slurry was concentrated and dried at 120° C for 12 hours and the dried product was calcinated at 420° C to yield a solid having the atomic ratio values indicated by the formula $Mo_{12}P_1Cs_2Sn_1O_{42}$. The solid was passed through a sieve to yield catalyst particles of 35 – 100 mesh. A U-shaped reactor made of stainless steel having an inner diameter of 8 mm was filled with the catalyst particles. A gaseous mixture composed of 4% of methacrolein; 10% of oxygen; 30% of steam; and 56% of nitrogen (percent by volume) was passed through the reactor with a contact time of 4 seconds at 340° C. The following results were obtained.

| | |
|---|---|
| Conversion of methacrolein (%) | 74% |
| Selectivity to methacrylic acid (%) | 76% |
| Selectivity to acetic acid (%) | 7% |

The lifetime of the catalyst was quite long.

REFERENCE A

Catalysts were prepared in accordance with the process of Example 1, except using either no cesium nitrate or no stannous chloride. The solid obtained possessed the atomic ratio values corresponding to the following formulas: $Mo_{12}P_1Sn_1O_{42}$ or $Mo_{12}P_1Cs_2O_{40}$. The reaction of Example 1 was repeated by using these catalysts. The results were as follows.

| | $Mo_{12}P_1Sn_1O_{42}$ | $Mo_{12}P_1Cs_2O_{40}$ |
|---|---|---|
| Conversion of methacrolein (%) | 43% | 42% |
| Selectivity to methacrylic acid (%) | 38% | 68% |
| Selectivity to acetic acid (%) | 5% | 8% |

EXAMPLE 2

A solution of 9.8 g of cesium nitrate and 2.0 g of ammonium nitrate in 50 cc of water was added with stirring to a solution of 58 g of phosphomolybdic acid dissolved in 50 cc of water. A solution of 5.6 g of stannous chloride in 20 cc of conc. HCl and 40 cc of water was added to the resulting solution. A solution of 7.2 g of nickel nitrate was added to the solution and the mixture was heated with stirring to form a slurry. The slurry was concentrated and dried at 120° C for 12 hours and the dried product was calcined at 420° C to yield a solid having atomic ratio values corresponding to the formula $Mo_{12}P_1Cs_2Sn_1NiO_{43}$. The solid was passed through a sieve to yield catalyst particles of 35 – 100 mesh. A U-shaped reactor made of stainless steel having an inner diameter of 8 mm was filled with the catalyst particles. A gaseous mixture composed of 4% of methacrolein; 10% of oxygen; 30% of steam and 56% of nitrogen (percent by volume) was passed through the reactor with the contact time of 4 seconds, at 340° C for 4 hours. The following results were obtained.

| | |
|---|---|
| Conversion of methacrolein (%) | 88% |
| Selectivity to methacrylic acid (%) | 78% |
| Selectivity to acetic acid (%) | 8% |

Examples 3 – 9

Catalysts were prepared in accordance with the process pf Example 2, except that 7.8 g of cobalt nitrate; 3.0 g of ammonium metavanadate; 3.2 g of selenious acid, 5.8 g of tungsten oxide; 10.2 g of ferric nitrate; 8.8 g of indium nitrate and 3.3 g of niobium pentaoxide used alternately instead of nickel nitrate, so as to give the atomic ratio values shown by the formulas in Table 1. The reaction of Example 1 was repeated using these catalysts. The results are also shown in Table 1.

Table 1

| Example No. | Catalysts | Methacrolein conversion (%) | Methacrylic acid selectivity (%) | Acetic acid selectivity (%) |
|---|---|---|---|---|
| 3 | $Mo_{12}P_1Cs_2Sn_1Co_1O_{44}$ | 78 | 73 | 9 |
| 4 | $Mo_{12}P_1Cs_2Sn_1V_1O_{45}$ | 93 | 82 | 7 |
| 5 | $Mo_{12}P_1Cs_2Sn_1Se_1O_{44}$ | 80 | 52 | 6 |
| 6 | $M_{12}P_1Cs_2Sn_1W_1O_{45}$ | 75 | 67 | 4 |
| 7 | $Mo_{12}P_1Cs_2Sn_1Fe_1O_{44}$ | 71 | 65 | 5 |
| 8 | $Mo_{12}P_1Cs_2Sn_1In_1O_{44}$ | 82 | 74 | 7 |
| 9 | $Mo_{12}P_1Cs_2Sn_1Nb_1O_{45}$ | 80 | 64 | 11 |

EXAMPLES 10–15

Catalysts were prepared in accordance with Examples 3–9 having atomic ratio values shown by the formulas in Table 2. The reaction of Example 1 was repeated using these catalysts. The results are also shown in Table 2.

Table 2

| Example No. | Catalysts | Methacrolein conversion (%) | Methacrylic acid selectivity (%) | Acetic acid selectivity (%) |
|---|---|---|---|---|
| 10 | $Mo_{12}P_{0.5}Cs_2Sn_1O_{38}$ | 68 | 69 | 5 |
| 11 | $Mo_{12}P_1Cs_7Sn_1Co_1O_{46}$ | 64 | 70 | 7 |
| 12 | $Mo_{12}P_1Cs_2Sn_5V_{0.5}O_{51}$ | 97 | 72 | 4 |
| 13 | $Mo_{12}P_2Cs_2Sn_1Fe_5O_{50}$ | 82 | 63 | 3 |
| 14 | $Mo_{12}P_{0.5}Cs_{0.5}Sn_{0.5}Nb_1O_{42}$ | 73 | 59 | 10 |
| 15 | $Mo_{12}P_1Cs_2Sn_1In_{0.5}O_{43}$ | 85 | 67 | 8 |

The lifetimes of the catalysts of Examples 2–15 were quite long.

EXAMPLE 16

A solution of 13.4 g of thallium nitrate and 2.0 of ammonium nitrate in 50 cc of water was added with stirring to a solution of 58 g of phosphomolybdic acid dissolved in 50 cc of water. A 3.0 sample of zirconium oxide was added to the resulting solution. The mixture was heated with stirring to form a slurry. The slurry was repeated using these catalysts. The results are also shown in Table 3.

Table 3

| Example No. | Catalysts | Methacrolein conversion (%) | Methacrylic acid selectivity (%) | Acetic acid selectivity (%) |
|---|---|---|---|---|
| 17 | $Tl_2Mo_{12}Nb_1P_1O_{43}$ | 70 | 75 | 4 |
| 18 | $Tl_2Mo_{12}Ni_1P_1O_{41}$ | 65 | 71 | 3 |
| 19 | $Tl_2Mo_{12}In_1P_1O_{42}$ | 90 | 78 | 2 |
| 20 | $Tl_2Mo_{12}Zr_1Nb_1P_1O_{45}$ | 77 | 78 | 9 |
| 21 | $Tl_2Mo_{12}Zr_1Ni_1P_1O_{43}$ | 71 | 79 | 4 |
| 22 | $Tl_2Mo_{12}Zr_1In_1P_1O_{44}$ | 65 | 79 | 8 |
| 23 | $Tl_2Mo_{12}Nb_1Ni_1P_1O_{44}$ | 77 | 77 | 7 |
| 24 | $Tl_2Mo_{12}Nb_1In_1P_1O_{44}$ | 97 | 68 | 6 |
| 25 | $Tl_2Mo_{12}In_1Ni_1P_1O_{43}$ | 81 | 71 | 5 |
| 26 | $Tl_2Mo_{12}Ba_1Zr_1P_1O_{43}$ | 86 | 80 | 10 |
| 27 | $Tl_2Mo_{12}Ba_1Nb_1P_1O_{44}$ | 73 | 71 | 6 |
| 28 | $Tl_2Mo_{12}Ba_1Ni_1P_1O_{42}$ | 73 | 82 | 7 |
| 29 | $Tl_2Mo_{12}Ba_1In_1P_1O_{43}$ | 90 | 65 | 14 |
| 30 | $Tl_2Mo_{12}Ba_1P_1O_{41}$ | 84 | 73 | 9 |
| 31 | $Tl_2Mo_{12}Zr_3P_1O_{46}$ | 70 | 65 | 7 |
| 32 | $Tl_7Mo_{12}Nb_1P_1O_{45}$ | 59 | 60 | 5 |
| 33 | $Tl_2Mo_{12}Zr_1Ni_5P_1O_{47}$ | 63 | 63 | 4 |
| 34 | $Tl_2Mo_{12}Nb_1In_3P_2O_{47}$ | 71 | 55 | 9 |
| 35 | $Tl_1Mo_{12}Ba_2Zr_1P_{0.5}O_{42}$ | 76 | 70 | 5 |
| 36 | $Tl_2Mo_{12}Ba_{0.5}In_{0.5}P_1O_{41}$ | 80 | 60 | 7 | concentrated and dried at 120° C for 12 hours and the dried product was calcined at at 420° C for 6 hours to yield a solid having the atomic ratio values corresponding to the formula $Mo_{12}P_1Tl_2ZrO_{42}$. The solid was passed through a sieve to yield catalyst particles of 35 — 100 mesh. A U-shaped reactor made of stainless steel having an inner diameter of 8 mm was filled with the catalyst particles. A gaseous mixture composed of 4% of methacrolein; 10% of oxygen; 30% of steam and 56% of nitrogen (percent by volume) was passed through the reactor with a contact time of 4 seconds at 340° C. The following results were obtained.

| | |
|---|---|
| Conversion of methacrolein (%) | 86% |
| Selectivity of methacrylic acid (%) | 71% |
| Selectivity of acetic acid (%) | 7% |

REFERENCE B

Catalysts were prepared in accordance with the process of Example 16, except that either no thallium nitrate or no zirconium oxide were used so as to yield a solid having the atomic ratio values corresponding to the formula $Mo_{12}P_1Zr_1O_{42}$ or $Mo_{12}P_1Tl_2O_{40}$. The reaction of Example 16 was repeated using these catalysts. The results are shown as follows.

| | $Mo_{12}P_1Zr_1O_{42}$ | $Mo_{12}P_1Tl_2O_{40}$ |
|---|---|---|
| Conversion of methacrolein (%) | 53% | 64% |
| Selectivity to methacrylic acid (%) | 27% | 35% |
| Selectivity to acetic acid (%) | 4% | 4% |

EXAMPLES 17 – 36

Catalysts were prepared in accordance with the process of Example 16, except that 3.3 g of niobium pentaoxide; 3.6 g of nickel nitrate; 3.8 g of barium oxide; 8.8 g of indium nitrate or various combinations of these were alternately used instead of zirconium oxide, yielding solids having the atomic ratio values shown by the formulas in Table 3. The reaction of Example 16 was

EXAMPLE 37

A soluton of 13.4 g of thallium nitrate and 2.0 of ammonium nitrate in 50 cc of water was added with stirring to a solution of 58 g of phosphomolybdic acid dissolved in 50 cc of water. A 3.0 g sample of zirconium oxide and 10.2 g of ferric nitrate were added to the resulting solution, and the mixture was heated with stirring to form a slurry. The slurry was concentrated and dried at 120° C for 12 hours and the dried product was calcined at 420° C for 6 hours to yield a solid having the atomic ratio values corresponding to the formula $Mo_{12}P_1Tl_2Zr_1Fe_1O_{44}$. The solid was passed through a sieve to yield catalyst particles of 35 – 100 mesh. A U-shaped reactor made of stainless steel having an inner diameter of 8 mm was filled with the catalyst particles. The reaction of Example 16 was repeated using these catalysts. The following results were obtained.

| | |
|---|---|
| Conversion of methacrolein (%) | 74% |
| Selectivity of methacrylic acid (%) | 76% |
| Selectivity of acetic acid (%) | 7% |

EXAMPLES 38–57

Catalysts were prepared in accordance with the process of Examples 37 except that 3.3 g of niobium pentaoxide; 3.6 g of nickel nitrate or 8.8 g of indium nitrate were alternately used instead of zirconium oxide; or that 3.0 g of ammonium metavanadate; 3.8 g of barium oxide; 3.2 g of selenious acid or 3.8 g of tin oxide instead of ferric nitrate, yielding solids having the atomic ratio values shown by the formulas in Table 4. The reaction of Example 37 was repeated using these catalysts. The results are also shown in Table 4.

EXAMPLE 58

A solution of 9.8 g of cesium nitrate and 2.0 g of ammonium nitrate in 50 cc of water was added with stirring to a solution of 58 g of phosphomolybdic acid dissolved in 50 cc of water. A solution of 3.0 g of ammonium metavanadate in 100 cc of water was added to the resulting solution. The mixture was heated with stirring to form a slurry. The slurry was concentrated and dried at 120° C for 12 hours and the dried product was calcined at 420° C to yield a solid having the atomic ratio values corresponding to the formula $Mo_{12}P_1Cs_2V_1O_{43}$. The solid was passed through a sieve to yield catalyst particles of 35 – 100 mesh.

sieve to yield catalyst particles of 35 – 100 mesh. A U-shaped reactor made of stainless steel having an inner diameter of 8 mm was filled with the catalysts particles. A gaseous mixture composed of 4% of methacrolein; 10% of oxygen; 30% of steam and 56% of nitrogen (percent by volume) was passed through the reactor with the contact time of 4 seconds, at 340° C Table 4

| Example No. | Catalysts | Methacrolein conversion (%) | Methacrylic acid selectivity (%) | Acetic acid selectivity (%) |
|---|---|---|---|---|
| 38 | $Tl_2Mo_{12}Zr_1V_1P_1O_{45}$ | 83 | 72 | 7 |
| 39 | $Tl_2Mo_{12}Zr_1Se_1P_1O_{44}$ | 66 | 85 | 4 |
| 40 | $Tl_2Mo_{12}Zr_1Sn_1P_1O_{44}$ | 60 | 83 | 5 |
| 41 | $Tl_2Mo_{12}Nb_1Fe_1P_1O_{44}$ | 78 | 84 | 9 |
| 42 | $Tl_2Mo_{12}Nb_1V_1P_1O_{45}$ | 86 | 78 | 7 |
| 43 | $Tl_2Mo_{12}Nb_1Se_1P_1O_{45}$ | 89 | 75 | 8 |
| 44 | $Tl_2Mo_{12}Nb_1Sn_1P_1O_{45}$ | 77 | 79 | 10 |
| 45 | $Tl_2Mo_{12}Ni_1Fe_1P_1O_{43}$ | 87 | 73 | 11 |
| 46 | $Tl_2Mo_{12}Ni_1V_1P_1O_{44}$ | 70 | 76 | 3 |
| 47 | $Tl_2Mo_{12}Ni_1Se_1P_1O_{43}$ | 78 | 77 | 4 |
| 48 | $Tl_2Mo_{12}Ni_1Sn_1P_1O_{43}$ | 91 | 71 | 5 |
| 49 | $Tl_2Mo_{12}In_1Fe_1P_1O_{43}$ | 75 | 74 | 13 |
| 50 | $Tl_2Mo_{12}In_1V_1P_1O_{44}$ | 74 | 72 | 8 |
| 51 | $Tl_2Mo_{12}In_1Se_1P_1O_{44}$ | 84 | 77 | 10 |
| 52 | $Tl_2Mo_{12}In_1Sn_1P_1O_{44}$ | 95 | 81 | 7 |
| 53 | $Mo_{12}P_1Tl_5Zr_1V_1O_{46}$ | 63 | 57 | 5 |
| 54 | $Mo_{12}P_3Tl_2Nb_1V_1O_{50}$ | 66 | 82 | 7 |
| 55 | $Mo_{12}P_1Tl_2Ni_1Fe_3O_{46}$ | 82 | 63 | 10 |
| 56 | $Mo_{12}P_1Tl_2In_5Fe_1O_{49}$ | 71 | 64 | 13 |
| 57 | $Mo_{12}P_1Tl_2In_1Sn_5O_{52}$ | 85 | 72 | 5 |

A U-shaped reactor made of stainless steel having an inner diameter of 8 mm was filled with the catalyst particles. A gaseous mixture composed of 4% of methacrolein; 10% of oxygen; 30% of steam and 56% of nitrogen (percent by volume) was passed through the reactor with the contact time of 4 seconds, at 340° C for 4 hours. The following results were obtained.

| | |
|---|---|
| Conversion of methacrolein (%) | 65% |
| Selectivity to methacrylic acid (%) | 75% |
| Selectivity to acetic acid (%) | 4% |

EXAMPLE 59

A solution of 9.8 g of cesium nitrate and 2.0 g of ammonium nitrate in 50 cc of water was added with stirring to a solution of 58 g of phosphomolybdic acid dissolved in 50 cc of water. A solution of 3.0 g of ammonium metavanadate in 100 cc of water was added to the resulting solution. The mixture was heated with stirring to form a slurry. The slurry was concentrated and the dried at 120° C for 12 hours and the dried product was calcined at 420° C to yield a solid having the atomic ratio values corresponding to the formula $Mo_{12}P_1Cs_2V_1W_1O_{46}$. The solid was passed through a for 4 hours. The following results were obtained.

| | |
|---|---|
| Conversion of methacrolein (%) | 71% |
| Selectivity to methacrylic acid (%) | 77% |
| Selectivity to acetic acid (%) | 6% |

EXAMPLES 60–67

Catalysts were prepared in accordance with the process of Example 59, except that 3.0 g of zirconium oxide; 7.8 g of cobalt nitrate; 7.2 g of nickel nitrate; 3.2 g of selenious acid; 10.2 g of ferric nitrate; 8.8 g of indium nitrate; 3.3 g of niobium pentaoxide or 3.8 g of barium oxide were alternately used instead of tungsten oxide, producing solids having the atomic ratio values shown by the formulas in Table 5. The reaction of Example 59 was repeated using these catalysts. The results are also shown in Table 5.

Table 5

| Example No. | Catalysts | Methacrolein conversion (%) | Methacrylic acid selectivity (%) | Acetic acid selectivity (%) |
|---|---|---|---|---|
| 60 | $Cs_2Mo_{12}V_1Zr_1P_1O_{45}$ | 76 | 79 | 8 |
| 61 | $Cs_2Mo_{12}V_1Co_1P_1O_{44}$ | 96 | 59 | 10 |
| 62 | $Cs_2Mo_{12}V_1Ni_1P_1O_{44}$ | 71 | 70 | 3 |
| 63 | $Cs_2Mo_{12}V_1Se_1P_1O_{45}$ | 75 | 69 | 5 |
| 64 | $Cs_2Mo_{12}V_1Fe_1P_1O_{44}$ | 96 | 66 | 11 |
| 65 | $Cs_2Mo_{12}V_1In_1P_1O_{44}$ | 100 | 57 | 15 |
| 66 | $Cs_2Mo_{12}V_1Nb_1P_1O_{45}$ | 87 | 71 | 6 |
| 67 | $Cs_2Mo_{12}V_1Ba_1P_1O_{44}$ | 75 | 80 | 5 |

REFERENCE C

Catalysts were prepared in accordance with the process of Example 58, except that either no cesium nitrate or no ammonium metavanadate were used. Solids were produced having the atomic ratio values corresponding to the formulas: $Mo_{12}P_1V_1O_{43}$ or $Mo_{12}P_1Cs_2O_{40}$. The reaction of Example 58 was repeated using these catalysts. The results were as follows.

|  | $Mo_{12}P_1V_1O_{43}$ | $Mo_{12}P_1Cs_2O_{40}$ |
|---|---|---|
| Conversion of methacrolein (%) | 47% | 42% |
| Selectivity to methacrylic acid (%) | 56% | 68% |
| Selectivity to acetic acid (%) | 7% | 8% |

Examples 68 – 73

Catalysts were prepared in accordance with the processes of Examples 58 and 59 except changing the amounts of the source materials for the metal components. The reaction of Example 58 was repeated using these catalysts. The results are shown in Table 6.

Table 6

| Example No. | Catalysts | Methacrolein conversion (%) | Methacrylic acid selectivity (%) | Acetic acid selectivity (%) |
|---|---|---|---|---|
| 68 | $Mo_{12}P_{0.5}Cs_2V_1O_{41}$ | 72 | 67 | 4 |
| 69 | $Mo_{12}P_1Cs_7V_1Co_1O_{46}$ | 68 | 68 | 8 |
| 70 | $Mo_{12}P_1Cs_2V_5W_1O_{56}$ | 67 | 74 | 6 |
| 71 | $Mo_{12}P_2Cs_2V_1Fe_6O_{52}$ | 66 | 69 | 3 |
| 72 | $Mo_{12}P_{0.5}Cs_{0.5}V_{0.5}Nb_1O_{42}$ | 77 | 67 | 10 |
| 73 | $Mo_{12}P_1Cs_2V_1In_{0.5}O_{44}$ | 81 | 62 | 5 |

In order to study the structure of the catalysts of the examples, X-ray diffraction and infrared spectra analysis have been conducted. In all of the examples, the catalysts containing cesium had a structure composed of cesium phosphomolybdate. The catalyst containing thallium had a structure composed of thallium phosphomolybdate. In Example 1 and Example 16, the reactions were continued for long periods (1, 60 and 120 days) in order to test the lifetime of the catalysts. The results are shown in Table 7 and Table 8.

Table 7

| Reaction time (days) | Reaction temperature (° C) | Methacrolein conversion (%) | Methacrylic acid selectivity (%) | Acetic acid selectivity (%) |
|---|---|---|---|---|
| 1 | 340 | 74 | 76 | 7 |
| 60 | 340 | 73 | 77 | 8 |
| 120 | 340 | 74 | 75 | 6 |

Table 8

| Reaction time (days) | Reaction temperature (° C) | Methacrolein conversion (%) | Methacrylic acid selectivity (%) | Acetic acid selectivity (%) |
|---|---|---|---|---|
| 1 | 340 | 86 | 71 | 7 |
| 60 | 340 | 85 | 72 | 8 |
| 120 | 340 | 86 | 71 | 9 |

As is clear from the results, the lifetimes of the catalysts of the invention are long. That is, they maintain their catalytic activity for long periods of active use.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for preparing methacrylic acid which comprises reacting methacrolein with molecular oxygen in the vapor phase at a temperature of from 230° C to 450° C in the presence of a catalyst having the formula $$Mo_{12}P_{\alpha'} \quad Cs_{\beta'} \quad Sn_{\gamma'} \quad O_{\delta'}$$

wherein
$\alpha' = 0.1 - 3$;
$\beta' = 0.2 - 9$;
$\gamma' = 0.1 - 7$;
$\delta' = 36 - 100$.

2. A process for preparing methacrylic acid which comprises reacting methacrolein with molecular oxygen in the vapor phase at a temperature of from 230° C to 450° C in the presence of a catalyst having the formula $$Mo_{12}P_{\alpha'} \quad Cs_{\beta'} \quad Sn_{\gamma'} \quad Z'_{\epsilon'} \quad O_{\delta'}$$

wherein $\alpha' = 0.1 - 3$; $\beta' = 0.2 - 9$; $\gamma' = 0.1 - 7$; and Z' is at least one member of the group consisting of Ni, Co, Fe, V, Nb, Ta, Se, W and In; $\epsilon' = 0.1 - 7$ and $\delta' = 36 - 130$.

3. The process of claim 1, wherein the catalyst has a structure composed of cesium phosphomolybdate.

4. The process of claim 1, wherein the reaction pressure is from 0.5 to 40 atmospheres absolute.

5. The process of claim 1, wherein the molecular ratio of the oxygen reactant is from 0.1 to 10 relative to the amount of methacrolein.

6. The process of claim 1, wherein steam, present in a concentration of from 2 to 80% of the volume of the feed, is added to the reaction mixture.

7. The process of claim 1, wherein the catalysts is prepared by concentrating a suspension, having a pH of lower than 10, which contains the desired components, drying the resulting concentrate, calcining the dried product at a temperature of from 250° to 450° C for 1 to 48 hours in air and grinding said dried product into a mesh size ranging from 5 to 100.

* * * * *